(12) United States Patent
Sasaki et al.

(10) Patent No.: US 8,420,109 B2
(45) Date of Patent: Apr. 16, 2013

(54) OILY BASE FOR A COSMETIC AND A COSMETIC COMPRISING THE SAME

(75) Inventors: Naoki Sasaki, Chiba (JP); Yuki Kokeguchi, Narita (JP); Kiyotaka Kawai, Narita (JP)

(73) Assignee: Kokyo Alcohol Kogyo Co., Ltd., Chiba (JP)

( * ) Notice: Subject to any disclaimer, the term of this patent is extended or adjusted under 35 U.S.C. 154(b) by 82 days.

(21) Appl. No.: 12/850,831

(22) Filed: Aug. 5, 2010

(65) Prior Publication Data

US 2011/0034723 A1    Feb. 10, 2011

Related U.S. Application Data

(60) Provisional application No. 61/273,535, filed on Aug. 5, 2009.

(51) Int. Cl.
| | | |
|---|---|---|
| *A61K 8/02* | (2006.01) | |
| *A61K 8/92* | (2006.01) | |
| *A61Q 1/02* | (2006.01) | |
| *C07C 69/66* | (2006.01) | |

(52) U.S. Cl.
USPC ........... 424/401; 424/64; 424/70.1; 424/70.7; 560/186

(58) Field of Classification Search .................. None
See application file for complete search history.

(56) References Cited

U.S. PATENT DOCUMENTS

| | | | | |
|---|---|---|---|---|
| 2004/0241198 | A1* | 12/2004 | Blin et al. | 424/401 |
| 2006/0083703 | A1 | 4/2006 | Torgerson | |
| 2010/0324136 | A1* | 12/2010 | Arahira et al. | 514/547 |

FOREIGN PATENT DOCUMENTS

| | | |
|---|---|---|
| JP | 50-76238 | 6/1975 |
| JP | 54-106415 | 8/1979 |
| JP | 55-085509 | 6/1980 |
| JP | 2006-045102 | 2/2006 |
| JP | 2006-111543 | 4/2006 |
| JP | 2007-84505 | 4/2007 |
| JP | 2008-516988 | 5/2008 |
| WO | WO-2006/003992 | 1/2006 |

* cited by examiner

*Primary Examiner* — Lakshmi Channavajjala
(74) *Attorney, Agent, or Firm* — Jordan and Hamburg LLP

(57) ABSTRACT

The present invention provides an oily base for a cosmetic comprising an ester compound made from a multivalent alcohol and a fatty acid, characterized in that the ester compound is made from dipentaerythritol and at least one fatty acid selected from the group consisting of fatty acids having 5 to 16 carbon atoms and a molar ratio of a dipentaerythritol residue to a fatty acid residue having 5 to 16 carbon atoms in the ester compound is 1.0:3.0 to 1.0:6.0. The aforesaid oily base for a cosmetic has proper oily feeling with moistness, no uncomfortable sticky feeling, excellent safety to the skin and adhesion to the skin, excellent gloss-holding ability after application to the skin, and excellent compatibility with various oil agents. In addition, upon blending the ester compound in various cosmetics, the cosmetics also have proper emollient property.

16 Claims, No Drawings

OILY BASE FOR A COSMETIC AND A COSMETIC COMPRISING THE SAME

BACKGROUND OF THE INVENTION

The present invention relates to an oily base for a cosmetic comprising an ester compound made from a multivalent alcohol and a fatty acid, and a cosmetic comprising the same, more specifically to an oily base for a cosmetic comprising an ester compound made from dipentaerythritol and a fatty acid having 5 to 16 carbon atoms, a cosmetic comprising the same, and a process for the preparation of the said ester compound.

In the prior art, various ester compounds are known as an oily base used in various cosmetics.

Document 1[*1] discloses a liquid ester composition obtained by esterifying dipentaerythritol with a branched type isostearic acid indicated by the chemical formula R—C(COOH)H—($CH_2CH_2$)—R, wherein R represents a branched hydrocarbon having 7 carbon atoms, characterized in that a viscosity of the composition at 25 degrees C. is 100,000 to 2,000,000 mPa·s, a hydroxyl value of the composition is 10 to 160, and a clouding point of the composition is less than 5 degrees C. The aforesaid liquid ester composition is obtained by reacting dipentaerythritol with stearic acid, which has 18 carbon atoms, having a particular branched structure. The aforesaid liquid ester composition exhibits excellent cosmetic film-holding ability and provides a cosmetic film having a gloss and moisturizing feeling comparable to polybutene which has been usually used in a cosmetic. In addition, the composition exhibits pigment-dispersing ability and water-holding property which polybutene does not have. Upon blending the aforesaid liquid ester composition in a make-up cosmetic, the effect is exhibited that the makeup cosmetic exhibits excellent cosmetic film-holding ability.

Document 2[*2] discloses an oily cosmetic comprising (A) a liquid ester composition obtained by esterifying a branched type isostearic acid represented by the general formula $R^1$—C(COOH)H—$CH_2CH_2$—$R^2$, wherein $R^1$ and $R^2$ represent a branched hydrocarbon radical having 7 carbon atoms and may be the same or different from each other, and (B) a silicone resin. As component (A), mention is made of dipentaerythrityl pentaisostearate, dipentaerythrityl tetraisostearate, dipentaerythrityl triisostearate, glyceryl triisostearate and diglyceryl triisostearate. As component (B), trimethylsiloxysilicic acid and perfluoroalkyl-polyalkylsiloxysilicic acid are mentioned. The invention described in Document 2 provides an oily cosmetic having comfortable feeling and good gloss when the cosmetic is applied, and excellent moisturizing feeling-holding ability and excellent cosmetic effect-holding ability.

Document 3[*3] discloses a cosmetic for lips comprising (A) a fluorine-polyether co-modified silicone and (B) a liquid ester composition obtained by esterifying dipentaerythritol with a branched type isostearic acid represented by the general formula $R^6$—C(COOH)H—$CH_2CH_2$—$R^7$, wherein $R^6$ and $R^7$ represent a branched hydrocarbon radical having 7 carbon atoms and may be the same or different from each other, wherein a viscosity at 25 degrees C. of the liquid ester composition is 100,000 to 2,000,000 mPa·s, a hydroxyl value of the liquid ester composition is 10 to 160, and a clouding point of the liquid ester composition is less than 5 degrees C. The ester composition of component (B) is the same as the ester composition described in Document 1. By blending a combination of the aforesaid component (B) with the aforesaid component (A) in a cosmetic for lips, the invention described in Document 3 gives excellent pigment-dispersing ability, excellent comfortable feeling on use and gloss when the cosmetic is applied, excellent moisturizing feeling-holding ability and excellent cosmetic effect-holding ability to the cosmetic for lips.

All the inventions described in the aforesaid Documents 1 to 3 use the composition wherein isostearic acid, which has 18 carbon atoms, having a particular branched structure is esterified. The resultant liquid ester composition has extremely high viscosity, which causes the problem that uncomfortable sticky feeling appears on the skin upon blending the composition in a skin-care cosmetic. Furthermore, another problem occurs, that is, the use of such a special substance raises the preparation cost.

Document 4[*4] discloses an oily composition for the skin comprising a co-enzyme represented by a particular formula and a medium chain fatty acid ester obtained by esterifying a medium chain fatty acid having 6 to 12 carbon atoms with a branched multivalent alcohol, and being free from water. The invention described in Document 4 provides an oily composition for the skin wherein the co-enzyme is able to be homogenously dissolved without crystallization or aggregation when the composition is prepared, having no problem in the safety to the skin and the stability, exhibiting good feeling on use when the composition is applied to the skin, and being highly effective to improve taut skin, wrinkle and sag. As the branched multivalent alcohol, mention is made of neopentyl glycol, pentaerythritol, dipentaerythritol, trimethylolpropane, ditrimethylolpropane and isopentyl glycol. There is a description that the particularly preferable branched multivalent alcohol is neopentyl glycol. As the medium chain fatty acid having 6 to 12 carbon atoms, mention is made of hexanoic acid, octanoic acid, nonanoic acid, decanoic acid, undecanoic acid, dodecanoic acid and 2-ethylhexanoic acid. In the Examples, as the medium chain fatty acid ester, only neopentyl glycol didecanoate, neopentyl glycol di2-ethylhexanoate and pentaerythrityl tetra2-ethylhexanoate are used.

The documents cited above are as follows:

*1 Document 1: WO 2006/3992 leaflet;
*2 Document 2: Japanese Patent Application Laid-Open 2006-111,543;
*3 Document 3: Japanese Patent Application Laid-Open 2006-45,102;
*4 Document 4: Japanese Patent Application Laid-Open 2007-84,505.

SUMMARY OF THE INVENTION

The present invention provides a novel oily base for a cosmetic comprising an ester compound which is made from dipentaerythritol and a fatty acid having 5 to 16 carbon atoms, and has a dipentaerythritol residue and a fatty acid residue having 5 to 16 carbon atoms in the predetermined molar ratio, and a cosmetic comprising the same.

In Documents 1 to 3 described above, there is disclosed a liquid ester composition obtained by reacting dipentaerythritol with a particular branched type isostearic acid. The ester composition is expected to have various effects upon blending it in a cosmetic. However, the ester composition has the drawbacks that uncomfortable sticky feeling appears on the skin when it is used in a skin-care cosmetic and that relatively high preparation cost is demanded. In Document 4, there is a description that the oily composition for the skin comprises a medium chain fatty acid ester obtained by esterifying a medium chain fatty acid having 6 to 12 carbon atoms with a branched multivalent alcohol. As the branched multivalent alcohol, mention is made of six kinds of alcohols, that is, neopentyl glycol, pentaerythritol, dipentaerythritol, trimethylolpropane, ditrimethylolpropane and isopentyl glycol. It is described that among these alcohols, neopentyl glycol is particularly preferable. Also in the Examples, mention is made of the embodiment in which a medium chain fatty acid ester obtained using neopentyl glycol is used. Although dipentaerythritol is also mentioned as the branched multivalent alcohol, in Document 4, there is a description that the effect of medium chain fatty acid esters obtained using dipentaerythritol is less than that of those obtained using neopentyl glycol. In addition, any medium chain fatty acid ester obtained using dipentaerythritol is used in no Example. Therefore, for the purpose of obtaining the cosmetics which have more excellent effects, no one has any incentive to select and use dipentaerythritol, which is said to have poor effects, among the branched multivalent alcohols described in Document 4.

The present inventors have made investigations to prepare more excellent ester compounds which may be used as an oily base for a cosmetic more easily and inexpensively. As a result, among many known raw materials for the preparation of an ester in the prior art, as a fatty acid, we have noticed a fatty acid having the predetermined carbon atoms mentioned below, which is used widely and is easily available, and used it in place of the isostearic acid, which has 18 carbon atoms, having a particular branched structure as described in Documents 1 to 3. As a multivalent alcohol, we have noticed dipentaerythritol which was described to be not very preferable as a raw material for the preparation of the medium chain fatty acid ester in Document 4. We have found that upon reacting the aforesaid fatty acid with dipentaerythritol in the predetermined molar ratio to prepare an ester compound, the resultant ester compound has proper oily feeling with moistness, no uncomfortable sticky feeling, excellent safety to the skin and adhesion to the skin, excellent gloss-holding ability after applied to the skin, and excellent compatibility with various oil agents. In addition, we have also found that upon blending the aforesaid ester compound in various cosmetics, besides having proper emollient and moisturizing property as well as proper oily feeling without uncomfortable sticky feeling, the cosmetic exhibits excellent gloss-holding ability, smooth feeling on use, excellent adhesion to the skin and safety to the skin, excellent cosmetic effect-holding property, and storage stability. It has not been known that an oily base for a cosmetic comprising at least one of the ester compounds obtained by reacting dipentaerythritol with the fatty acid having the predetermined number of carbon atom in the predetermined molar ratio has the various effects mentioned above, which is new knowledge.

Thus, the present invention is (1) an oily base for a cosmetic comprising an ester compound made from a multivalent alcohol and a fatty acid, characterized in that the ester compound is made from dipentaerythritol and at least one fatty acid selected from the group consisting of fatty acids having 5 to 16 carbon atoms and a molar ratio of a dipentaerythritol residue to a fatty acid residue having 5 to 16 carbon atoms in the ester compound is 1.0:3.0 to 1.0:6.0.

As preferred embodiments of the present invention, mention may be made of (2) the oily base for a cosmetic according to the above (1), wherein the molar ratio of a dipentaerythritol residue to a fatty acid residue having 5 to 16 carbon atoms is 1.0:3.5 to 1.0:6.0;

(3) the oily base for a cosmetic according to the above (1), wherein the molar ratio of a dipentaerythritol residue to a fatty acid residue having 5 to 16 carbon atoms is 1.0:4.0 to 1.0:6.0;

(4) the oily base for a cosmetic according to any one of the above embodiments (1) to (3), wherein the fatty acid has 8 to 16 carbon atoms;

(5) the oily base for a cosmetic according to any one of the above embodiments (1) to (3), wherein the fatty acid has 9 to 16 carbon atoms;

(6) the oily base for a cosmetic according to any one of the above embodiments (1) to (3), wherein the fatty acid is selected from the group consisting of isononanoic acid, neopentanoic acid, 2-ethylhexanoic acid, neodecanoic acid, isomyristic acid and isopalmitic acid;

(7) the oily base for a cosmetic according to any one of the above embodiments (1) to (3), wherein the fatty acid is isononanoic acid;

(8) the oily base for a cosmetic according to any one of the above embodiments (1) to (7), wherein a hydroxyl value of the oily base is 0 to 340;

(9) the oily base for a cosmetic according to any one of the above embodiments (1) to (7), wherein a hydroxyl value of the oily base is 0.5 to 200;

(10) the oily base for a cosmetic according to any one of the above embodiments (1) to (7), wherein a hydroxyl value of the oily base is 0.5 to 150;

(11) the oily base for a cosmetic according to any one of the above embodiments (1) to (10), wherein a saponification value of the oily base is 170 to 450;

(12) the oily base for a cosmetic according to any one of the above embodiments (1) to (10), wherein a saponification value of the oily base is 175 to 360;

(13) the oily base for a cosmetic according to any one of the above embodiments (1) to (10), wherein a saponification value of the oily base is 180 to 320;

(14) the oily base for a cosmetic according to any one of the above embodiments (1) to (13), wherein a viscosity at 25 degrees C. of the oily base is 500 to 40,000 mPa·s.;

(15) the oily base for a cosmetic according to any one of the above embodiments (1) to (13), wherein a viscosity at 25 degrees C. of the oily base is 500 to 24,000 mPa·s.;

(16) the oily base for a cosmetic according to any one of the above embodiments (1) to (13), wherein a viscosity at 25 degrees C. of the oily base is 500 to 20,000 mPa·s.;

(17) a cosmetic comprising the oily base for a cosmetic according to any one of the above embodiments (1) to (16);

(18) the oily base for a cosmetic according to any one of the above embodiments (1) to (16) for skin creams, hair treatments, foundations, mascaras, eye shadows, lip glosses or lipsticks. Another invention is

(19) a process for the preparation of an ester compound for an oily base for a cosmetic by reacting a multivalent alcohol and a fatty acid, characterized in that the multivalent alcohol is dipentaerythritol, the fatty acid is at least one selected from the group consisting of fatty acids having 5 to 16 carbon atoms and a molar ratio of dipentaerythritol to the fatty acid having 5 to 16 carbon atoms in the reaction is 1.0:3.0 to 1.0:6.0.

As preferred embodiments of the present invention, mention may be made of:

(20) the process according to the above (19), wherein the molar ratio of dipentaerythritol to the fatty acid having 5 to 16 carbon atoms is 1.0:3.5 to 1.0:6.0;

(21) the process according to the above (19), wherein the molar ratio of dipentaerythritol to the fatty acid having 5 to 16 carbon atoms is 1.0:4.0 to 1.0:6.0;

(22) the process according to any one of the above embodiments (19) to (21), wherein the fatty acid has 8 to 16 carbon atoms;

(23) the process according to any one of the above embodiments (19) to (21), wherein the fatty acid has 9 to 16 carbon atoms;

(24) the process according to any one of the above embodiments (19) to (21), wherein the fatty acid is selected from the group consisting of isononanoic acid, neopentanoic acid, 2-ethylhexanoic acid, neodecanoic acid, isomyristic acid and isopalmitic acid;

(25) the process according to any one of the above embodiments (19) to (21), wherein the fatty acid is isononanoic acid.

The oily base for a cosmetic of the present invention has proper oily feeling with moistness, no uncomfortable sticky feeling, excellent safety to the skin and adhesion to the skin, excellent gloss-holding ability after applied to the skin, and excellent compatibility with various oil agents. In addition, upon blending the ester compound in various cosmetics, besides having proper emollient and moisturizing property as well as proper oily feeling without uncomfortable sticky feeling, the cosmetic exhibits excellent gloss-holding ability, smooth feeling on use, excellent adhesion to the skin and safety to the skin, excellent cosmetic effect-holding property, and storage stability. For example, when the oily base is used in a skin-care cosmetic, the cosmetic has proper oily feeling with moistness, no uncomfortable sticky feeling and stimulus, excellent safety to the skin. When used in a hair-care cosmetic, besides having the same effects as the skin-care cosmetic, the hair-care cosmetic exhibits excellent affinity with the hair. When used in a makeup cosmetic, the cosmetic has proper oily feeling, no uncomfortable sticky feeling, good moisturizing feeling-holding ability, good spreading ability on the skin and good adhesion to the skin. Since the cosmetic exhibits excellent pigment-dispersing ability, even if the long time elapses after it is applied, individual oily sheen, which is usually seen in the prior art silicone oil-based cosmetics, does not easily appear, and the affinity with the skin is good and cosmetic creasing or make-up deterioration does not easily occur. When used in a cosmetic for lips, the cosmetic has proper oily feeling, no uncomfortable sticky feeling, and good moisturizing feeling-holding ability, and is smooth on lips with sliminess, and has excellent gloss-holding ability without muddy appearance due to saliva.

DETAILED DESCRIPTION OF THE INVENTION

The ester compound contained in the oily base for a cosmetic of the present invention is made from dipentaerythritol as a multivalent alcohol and at least one fatty acid selected from the group consisting of fatty acids having 5 to 16 carbon atoms, preferably 8 to 16 carbon atoms, and more preferably 9 to 16 carbon atoms. The fatty acid may be linear or branched, and saturated or unsaturated. For example, mention is made of n-pentanoic acid, neopentanoic acid, n-hexanoic acid, isohexanoic acid, octanoic acid, isononanoic acid, nonanoic acid, 2-ethylhexanoic acid, neodecanoic acid, isomyristic acid and isopalmitic acid. Among these, preference is given to isononanoic acid, neopentanoic acid, 2-ethylhexanoic acid, neodecanoic acid, isomyristic acid and isopalmitic acid, and isononanoic acid is more preferable.

A molar ratio of a dipentaerythritol residue to a fatty acid residue in the ester compound is 1.0:3.0 to 1.0:6.0, preferably 1.0:3.5 to 1.0:6.0, and more preferably 1.0:4.0 to 1.0:6.0. When the ratio of a fatty acid residue to a dipentaerythritol residue is below 3.0 in the preparation of the ester compound, for the purpose of obtaining the ester in which the molar ratio of the fatty acid residue is below the aforesaid lower limit, dipentaerythritol does not sufficiently react and, therefore, a large amount of unreacted dipentaerythritol, which is unnecessary, remains in the reaction product containing the ester compound. As a result, when the whole reaction product is used as an oily base for a cosmetic, the ester compound may not exhibit the effects of the present invention. The smaller the molar ratio of the fatty acid to dipentaerythritol is in the preparation of the ester compound, the more the effects of the present invention become lowered. When the molar ratio of the fatty acid to dipentaerythritol is not more than about 2.0, few ester compounds may be obtained due to the existence of excess dipentaerythritol.

The ester compound made from dipentaerythritol and the aforesaid fatty acid includes monoesters, diesters, triesters, tetraesters, pentaesters and hexaesters, of dipentaerythritol with the aforesaid fatty acid. The oily base for a cosmetic of the present invention comprises at least one, preferably at least two of the ester compound made from dipentaerythritol and the fatty acid having 5 to 16 carbon atoms.

The oily base for a cosmetic of the present invention may also comprise a substance produced in the preparation of the ester compound mentioned above as by-products and unreacted reactants, in addition to the aforesaid ester compound. The substance produced as by-products, which is not clearly identified, is presumed to be, for example, substances originated from raw materials, acid anhydrides, self-condensation products of dipentaerythritol, polymerization products of the esters, etc. The content of these substances, which varies depending on the molar ratio of dipentaerythritol to the fatty acid having 5 to 16 carbon atoms used in the reaction or the kind of the fatty acid, is preferably not more than 2.0% by mass in the oily base for a cosmetic. The oily base for a cosmetic of the present invention may be used without separating these by-products. Therefore, omitting operations for separation is advantageous. As a matter of course, the oily base may be used after these by-products are separated and removed.

The upper limit of a hydroxyl value of the oily base for a cosmetic comprising the ester compound of the present invention is preferably 340, more preferably 200, and further more preferably 150. The lower limit, which is not specifically decided, is preferably 0.5. When the hydroxyl value is beyond the upper limit, the compatibility with oil agents decreases, and when it is below the lower limit, the moisturizing property or the emollient property becomes poor.

The upper limit of a saponification value of the oily base for a cosmetic of the present invention is preferably 450, more preferably 360, and further more preferably 320. The lower limit is preferably 170, more preferably 175, and furthermore preferably 180. When the saponification value beyond the upper limit, the adhesion ability to the skin decreases, and when it is below the lower limit, uncomfortable sticky feeling appears upon application to the skin. These properties are not preferable for a cosmetic.

The upper limit of a viscosity at 25 degrees C. of the oily base for a cosmetic of the present invention is preferably 40,000 mPa·s., more preferably 24,000 mPa·s., and further more preferably 20,000 mPa·s. and the lower limit is preferably 500 mPa·s. When the viscosity is beyond the upper limit, the adhesion to the skin is too strong, and, therefore, uncomfortable sticky feeling appears upon application to the skin, and when it is below the lower limit, the adhesion ability to the skin decreases. These properties are not preferable for a cosmetic.

The oily base for a cosmetic of the present invention mentioned above may be used in various cosmetics such as skin creams, hair treatments, foundations, mascaras, eye shadows, lip glosses and lipsticks. The content of the oily base in the cosmetic, which depends on the kind of cosmetic, is preferably 0.1 to 80% by mass, more preferably 0.5 to 70% by mass, and further more preferably 0.5 to 60% by mass.

The ester compound contained in the oily base for a cosmetic of the present invention may be prepared by reacting dipentaerythritol with at least one fatty acid selected from the group consisting of fatty acids having 5 to 16 carbon atoms, preferably 8 to 16 carbon atoms, and more preferably 9 to 16 carbon atoms in a molar ratio of 1.0:3.0 to 1.0:6.0, preferably 1.0:3.5 to 1.0:6.0, more preferably 1.0:4.0 to 1.0:6.0. The fatty acid mentioned above may be used in this reaction. When the molar ratio of the fatty acid to dipentaerythritol is below 3.0, as described above, dipentaerythritol does not sufficiently react and, therefore, a large amount of unreacted dipentaerythritol, which is unnecessary, remains in the reaction product containing the ester compound. As a result, when the whole reaction product is used as an oily base for a cosmetic, the ester compound may not exhibit the effects of the present invention. The smaller the molar ratio of the fatty acid to dipentaerythritol is in the preparation of the ester compound, the more the effects of the present invention become lowered. When the molar ratio of the fatty acid to dipentaerythritol is not more than about 2.0, few ester compounds may be obtained due to the existence of excess dipentaerythritol. Meanwhile, it is possible to use excess amount of the fatty acid to dipentaerythritol. However, as the unreacted fatty acid contained in the reaction product may damage the properties of the ester compound, it is usually preferable to remove the unreacted fatty acid after the termination of the reaction. The reaction of dipentaerythritol with the aforesaid fatty acid may be carried out according to the process known in the prior art.

The oily base for a cosmetic comprising the ester compound of the present invention may be used in various cosmetics, for example, skin-care cosmetics such as skin creams, hair-care cosmetics such as hair treatments, makeup cosmetics such as foundations, mascaras and eye shadows, and cosmetics for lips such as lip glosses and lipsticks. Although the intact reaction product containing at least one ester compound as prepared above may be used as an oily base, if desired, use may also be made of the reaction product after removing impurities contained therein. Each cosmetic mentioned above may be prepared according to the process known in the prior art.

In the following Examples, the present invention will be described in more detail, but not limited thereto.

EXAMPLES

Preparation Examples and Comparative Preparation Examples

The substances used in the Preparation Examples and the Comparative Preparation Examples were as follows, unless otherwise stated;

Dipentaerythritol: Dipentaerythritol, trademark, from Koei Chemical Co. Ltd.

Isononanoic acid [$C(CH_3)_3CH_2CH(CH_3)CH_2COOH$]: Kyowanoic-N, trademark, from Kyowa Hakko Chemical Co. Ltd.

Neopentanoic acid [$(CH_3)_3CCOOH$]: Neopentanoic acid, trademark, from Exxon Mobil Corporation.

2-Ethylhexanoic acid[$CH_3(CH_2)_3CH(CH_2CH_3)COOH$]: Octylic acid, trademark, from Kyowa Hakko Chemical Co. Ltd.

Neodecanoic acid [$C_9H_{19}COOH$, mixture of structural isomers]: Neodecanoic acid, trademark, from Exxon Mobil Corporation.

Isomyristic acid [mixture of $CH_3CH(CH_3)(CH_2)_4CH[CH_3CH(CH_3)CH_2CH_2]COOH$ and $CH_3(CH_2)_2CH(CH_3)(CH_2)_2CH[CH_3(CH_2)_2CH(CH_3)]COOH$]: Isomyristic acid, trademark, from Nissan Chemical Industries, Ltd.

Isopalmitic acid [$CH_3(CH_2)_7CH(C_6H_{13})COOH$]: Isopahnitic acid, trademark, from Nissan Chemical Industries, Ltd.

Isobutanoic acid (isobutyric acid)[$(CH_3)_2CHCOOH$]: isobutyric acid, from OXEA Corporation Isostearic acid [$C_{17}H_{35}COOH$, mixture of structural isomers]: Isostearic acid EX, trademark, from Kokyu Alcohol Kogyo Co., Ltd.

Acid value, hydroxyl value, saponification value, viscosity, adhesion ability and gloss of the ester made from dipentaerythritol and the fatty acid obtained in the Preparation Examples and the Comparative Preparation Examples were determined as follows;

Acid value: determined in accordance with the method for the determination of an acid value described in "Japanese Standard of Cosmetic Ingredient, the 18$^{th}$ Acid Value".

Hydroxyl value: determined in accordance with the method for the determination of a hydroxyl value described in "Japanese Standard of Cosmetic Ingredient, the 24$^{th}$ Hydroxyl Value".

Saponification value: determined in accordance with the method for the determination of a saponification value described in "Japanese Standard of Cosmetic Ingredient, the 16$^{th}$ Saponification Value".

Viscosity: determined by Brookfield Viscometer DV-II+ (Spindle No. 3, 12 rpm, 25 degrees C.).

Adhesion ability: After 0.1 g of the ester, made from dipentaerythritol and the fatty acid, obtained in the Preparation Examples and the Comparative Preparation Examples was applied to the inner side of the upper arm, "adhesion ability" was evaluated by twenty panels. The indication of the evaluation results is as follows. When not less than 15 panels among 20 panels evaluated the compound as "good adhesion ability", it was rated as "G". When from 6 to 9 panels evaluated the compound as "good adhesion ability", it was rated as "M". When not more than five panels evaluated the cosmetic as "good adhesion ability", it was rated as "B".

Intrinsic gloss of the ester made from dipentaerythritol and the fatty acid:

About one gram of the ester made from dipentaerythritol and the fatty acid was applied in a thickness of about 200 μm on an area of about 20 mm in length and about 40 mm width on a sheet of waxed paper. Using a gloss checker IG-330, trademark, from Horiba Ltd., gloss was determined three times at an angle of incidence of 60 degrees and an angle of reflection of 60 degrees. The average value was used as gloss.

Gloss of the ester made from dipentaerythritol and the fatty acid upon contact with water Upon contact with saliva, the ester made from dipentaerythritol and the fatty acid becomes muddy and the gloss of the ester decreases. The decrease of gloss greatly influences the appearance. In order to evaluate the gloss in appearance, a transmittance of the ester made from dipentaerythritol and the fatty acid upon contact with water was used as an indicator of gloss. About one gram of the ester made from dipentaerythritol and the fatty acid was applied in a thickness of about 200 μm on an area of about 10 mm in length and about 20 mm in width on a plate made of quartz, after which 0.1 mL of purified water was put dropwise on the ester. After the ester made from dipentaerythritol and the fatty acid was lightly kneaded with water by fingers five times back and forth, the applied surface was smoothed with a spatula and then a transmittance, T %, was determined with a spectrophotometer for ultraviolet and visible region, UV-160A, trademark, from Shimadzu Corporation. The intrinsic transmittance of the ester made from dipentaerythritol and the fatty acid was represented as 100%, and then a transmittance of the ester upon contact with water was determined. "Gloss" was evaluated by the difference between both the transmittances. The transmittance here means average transmittance determined by scanning at a wave length of 400 to 800 nm.

Preparation Example 1

In a four-neck 3,000 mL flask equipped with a stirrer, a thermometer, a gas inlet tube, and a Dean-Stark condenser with a water measuring trap were placed 381.5 g (1.5 mol) of dipentaerythritol, 948 g (6.0 mol) of isononanoic acid (having 9 carbon atoms), 150 mL of toluene as a solvent and 4.0 g of paratoluenesulfonic acid as a catalyst. Next, the mixture was heated to 200 degrees C. under a flow of nitrogen gas in a rate of 20 mL/min. At the aforesaid temperature, the reaction took place while distilling off the produced water with the solvent azeotropically. When the distillation-off water subsided, the temperature was raised to 220 degrees C. to further continue the reaction. When the distillation-off water stopped, the reaction was terminated. It took about 20 hours from the start of the reaction to this point. Then, after the temperature was lowered to 180 degrees C., the pressure was reduced to about 20 mmHg to remove toluene, solvent, completely. The resultant reaction product was subjected to purification treatments of decolorization and deodorization according to the usual method. Then, 952.3 g of the ester made from dipentaerythritol and the fatty acid, pale yellow viscous oil, was obtained (acid value: 0.65, hydroxyl value: 125, and saponification value: 277.7).

The molar ratio of dipentaerythritol to isononanoic acid used in the reaction was 1.0:4.0.

To the ester made from dipentaerythritol and the fatty acid thus obtained, was added potassium hydroxide/ethanol solution to hydrolyze the ester. Next, the resultant hydrolyzation product was filtered to separate off the unsaponified product. After ethanol was removed from the filtrate, which was then acidified with hydrochloric acid, the saponified product was extracted with hexane. The unsaponified product and the saponified product were respectively silylated and methylated according to the usual method and then analyzed with gas chromatography (6890N from Agilent Technologies) to identify and quantitate the products. As a result, it was found that the ester obtained was made from dipentaerythritol and isononanoic acid, and the molar ratio of a dipentaerythritol residue to an isononanoic acid residue was 1.0:4.0.

Preparation Example 2

The procedures of Preparation Example 1 were repeated, except that the amount of isononanoic acid was changed to 1422 g (9.0 mol). 1392 g of the ester made from dipentaerythritol and the fatty acid, pale yellow highly viscous oil, was obtained (acid value: 0.02, hydroxyl value: 1.1, and saponification value: 303.5).

The molar ratio of dipentaerythritol to isononanoic acid used in the reaction was 1.0:6.0.

Preparation Example 3

The procedures of Preparation Example 1 were repeated, except that the amount of isononanoic acid was changed to 711 g (4.5 mol). 802 g of the ester made from dipentaerythritol and the fatty acid, pale yellow highly viscous oil, was obtained (acid value: 0.43, hydroxyl value: 226.1, and saponification value: 256.4).

The molar ratio of dipentaerythritol to isononanoic acid used in the reaction was 1.0:3.0.

Preparation Example 4

The procedures of Preparation Example 1 were repeated, except that 612.8 g (6.0 mole) of neopentanoic acid (having 5 carbon atoms) was used in place of isononanoic acid. 815 g of the ester made from dipentaerythritol and the fatty acid, pale yellow highly viscous oil, was obtained (acid value: 0.26, hydroxyl value: 171.3, and saponification value: 376.2).

The molar ratio of dipentaerythritol to neopentanoic acid used in the reaction was 1.0:4.0.

Preparation Example 5

The procedures of Preparation Example 1 were repeated, except that 865.3 g (6.0 mole) of 2-ethylhexanoic acid (having 8 carbon atoms) was used in place of isononanoic acid. 1034 g of the ester made from dipentaerythritol and the fatty acid, pale yellow highly viscous oil, was obtained (acid value: 0.48, hydroxyl value: 133.8, and saponification value: 298.3).

The molar ratio of dipentaerythritol to 2-ethylhexanoic acid used in the reaction was 1.0:4.0.

Preparation Example 6

The procedures of Preparation Example 1 were repeated, except that 1033.6 g (6.0 mole) of neodecanoic acid (having 10 carbon atoms) was used in place of isononanoic acid. 1032.5 g of the ester made from dipentaerythritol and the fatty acid, pale yellow highly viscous oil, was obtained (acid value: 0.39, hydroxyl value: 116.6, and saponification value: 259.8).

The molar ratio of dipentaerythritol to neodecanoic acid used in the reaction was 1.0:4.0.

Preparation Example 7

The procedures of Preparation Example 1 were repeated, except that 1370 g (6.0 mole) of isomyristic acid (having 14 carbon atoms) was used in place of isononanoic acid. 1347.9 g of the ester made from dipentaerythritol and the fatty acid, pale yellow highly viscous oil, was obtained (acid value: 0.67, hydroxyl value: 93.1, and saponification value: 204.2).

The molar ratio of dipentaerythritol to isomyristic acid used in the reaction was 1.0:4.0.

Preparation Example 8

The procedures of Preparation Example 1 were repeated, except that 1539 g (6.0 mole) of isopalmitic acid (having 16 carbon atoms) was used in place of isononanoic acid. 1431.9 g of the ester made from dipentaerythritol and the fatty acid, pale yellow highly viscous oil, was obtained (acid value: 0.92, hydroxyl value: 79.0, and saponification value: 182.4).

The molar ratio of dipentaerythritol to isopalmitic acid used in the reaction was 1.0:4.0.

Comparative Preparation Example 1

The procedures of Preparation Example 1 were repeated, except that the amount of isononanoic acid was changed to 474 g (3.0 mol). A large amount of unreacted dipentaerythritol remained and therefore the ester made from dipentaerythritol and the fatty acid was not able to be obtained.

The molar ratio of dipentaerythritol to isononanoic acid used in the reaction was 1.0:2.0.

Comparative Preparation Example 2

The procedures of Preparation Example 1 were repeated, except that 528.7 g (6.0 mol) of isobutanoic acid, isobutyric acid, (having 4 carbon atoms) was used in place of isononanoic acid. 665.8 g of the ester made from dipentaerythritol and the fatty acid, pale yellow highly viscous oil, was obtained (acid value: 0.15, hydroxyl value: 189.1, and saponification value: 420.3).

The molar ratio of dipentaerythritol to isobutanoic acid, isobutyric acid, used in the reaction was 1.0:4.0.

Comparative Preparation Example 3

The procedures of Preparation Example 1 were repeated, except that 1740 g (6.0 mol) of isostearic acid (having 18 carbon atoms) was used in place of isononanoic acid. 1671.2 g of the ester made from dipentaerythritol and the fatty acid, pale yellow highly viscous oil, was obtained (acid value: 0.05, hydroxyl value: 74.5, and saponification value: 169.7).

The molar ratio of dipentaerythritol to isostearic acid used in the reaction was 1.0:4.0.

Properties of each product obtained in the Preparation Examples and the Comparative Preparation Examples are shown in Table 1.

was small. The adhesion ability was also good. Also in the cases where neopentanoic acid, 2-ethylhexanoic acid, neodecanoic acid, isomyristic acid and isopalmitic acid were respectively used, the adhesion abilities were good, that is, did not deteriorate, and the glosses were good, that is, did not decrease, in all the esters when the molar ratio of the fatty acid to dipentaerythritol in the reaction was 1.0:3.0 to 1.0:6.0, as the case where isononanoic acid was used.

Meanwhile, in Comparative Preparation Example 1, the molar ratio of isononanoic acid, which was used in Preparation Example 1, was below the lower limit in the present invention. The ester made from dipentaerythritol and the fatty acid was not obtained because a large amount of unreacted dipentaerythritol remained. In Comparative Preparation Examples 2 and 3, isobutanoic acid, isobutyric acid, having 4 carbon atoms and isostearic acid having 18 carbon atoms, either of which has the number of carbon atom out of the present invention, were respectively used in place of isononanoic acid used in Preparation Example 1. In the ester made from dipentaerythritol and the fatty acid obtained in Comparative Preparation Example 2, the adhesion ability was considerably poor, and the odor and the safety to the skin were also poor. Here, the odor was estimated by organoleptic assessments. The safety to the skin was estimated according to the method in the Examples and the Comparative Examples described below using 0.05 g of the ester, made from dipentaerythritol and the fatty acid, obtained. In the

TABLE 1

| | Molar ratio in the reaction | | | Acid value | Hydroxyl value | Saponification value | Viscosity (mPa·s at 25° C.) | Adhesion ability | Gloss | |
| --- | --- | --- | --- | --- | --- | --- | --- | --- | --- | --- |
| | Dipentaerythritol | Fatty acid | Kind of fatty acid | | | | | | Intrinsic | Upon contact with water |
| Prep. Ex. 1 | 1.0 | 4.0 | Isononanoic acid | 0.65 | 125 | 277.7 | 15,550 | G | 78 | 96 |
| Prep. Ex. 2 | 1.0 | 6.0 | Isononanoic acid | 0.02 | 1.1 | 303.5 | 1,200 | G | 73 | 97 |
| Prep. Ex. 3 | 1.0 | 3.0 | Isononanoic acid | 0.43 | 226.1 | 256.4 | 25,000 | G | 74 | 92 |
| Prep. Ex. 4 | 1.0 | 4.0 | Neopentanoic acid | 0.26 | 171.3 | 376.2 | 19,400 | G | 74 | 91 |
| Prep. Ex. 5 | 1.0 | 4.0 | 2-Ethylhexanoic acid | 0.48 | 133.3 | 298.3 | 16,200 | G | 73 | 90 |
| Prep. Ex. 6 | 1.0 | 4.0 | Neodecanoic acid | 0.39 | 116.2 | 259.8 | 12600 | G | 73 | 91 |
| Prep. Ex. 7 | 1.0 | 4.0 | Isomyristic acid | 0.67 | 93.1 | 204.2 | 2400 | G | 73 | 90 |
| Prep. Ex. 8 | 1.0 | 4.0 | Isopalmitic acid | 0.92 | 79 | 182.4 | 800 | G | 73 | 90 |
| Com. Prep. Ex. 1 | 1.0 | 2.0 | Isononanoic acid | —*1 | —*1 | —*1 | —*1 | —*1 | —*1 | —*1 |
| Com. Prep. Ex. 2 | 1.0 | 4.0 | Isobutyric acid | 0.15 | 189.1 | 420.3 | 22,800 | B | 73 | 90 |
| Com. Prep. Ex. 3 | 1.0 | 4.0 | Isostearic acid | 0.05 | 74.5 | 169.7 | 1,900 | M | 74 | 36 |

In the above Table, *1 indicates that the ester made from dipentaerythritol and the fatty acid was not obtained because a large amount of unreacted dipentaerythritol remained.

In Preparation Examples 1 to 3, the molar ratio of isononanoic acid (having 9 carbon atoms) is varied within the present invention. The intrinsic gloss of the ester made from dipentaerythritol and the fatty acid was good and, in addition, the decrease of gloss upon contact with water was considerably small. The adhesion ability was also good. The viscosity of the ester was extremely low in Preparation Example 2. In Preparation Examples 4, 5, 6, 7 and 8, neopentanoic acid having 5 carbon atoms, 2-ethylhexanoic acid having 8 carbon atoms, neodecanoic acid having 10 carbon atoms, isomyristic acid having 14 carbon atoms, and isopalmitic acid having 16 carbon atoms were used respectively in place of isononanoic acid used in Preparation Example 1. In all the Preparation Examples, the resultant ester made from dipentaerythritol and the fatty acid sufficiently exhibited the effects of the present invention, although the gloss was somewhat lower than that in Preparation Example 1 where isononanoic acid was used, and the decrease of gloss upon contact with water ester, made from dipentaerythritol and the fatty acid, obtained in Comparative Preparation Example 3, the gloss upon contact with water was considerably poor. In addition, the adhesion ability was not good.

Examples and Comparative Examples

The substances used in the following Examples and Comparative Examples are as follows, unless otherwise stated:

Squalane: from Kokyu Alcohol Kogyo Co., Ltd., OLIVE SQUALANE;

Polyglyceryl-2 isostearate/dimer dilinoleate copolymer [0]: from Kokyu Alcohol Kogyo Co., Ltd., HAILUCENT ISDA, trademark;

Polyglyceryl-10 stearate: from Nikko Chemicals Co., Ltd., NIKKOL Decaglyn1-SV, trademark;

Polysorbate-80: from Kao Corporation, RHEODOL TW-0120V, trademark;

Hydrogenated lecithin: from Nikko Chemicals Co., Ltd., NIKKOL Lecinol S-10EX, trademark;

Behenyl alcohol: from Kokyu Alcohol Kogyo Co., Ltd., BEHENYL ALCOHOL 65, trademark;

Hydrogenated rapeseed alcohol: from Kokyu Alcohol Kogyo Co., Ltd., ALCOHOL No. 20-B, trademark;

Cetearyl alcohol: from Kokyu Alcohol Kogyo Co., Ltd., CETOSTEARYL ALCOHOL, trademark;

Pentylene glycol: from Kokyu Alcohol Kogyo Co., Ltd., DIOL PD, trademark;

Paraffin: from Ina Trading Co., Ltd., PARAFFIN WAX SP, trademark;

Dipropylene glycol (DPG): from Kuraray Co., Ltd., DPG-RF, trademark;

1,3-Butylene glycol (1,3-BG): from Kokyu Alcohol Kogyo Co., Ltd., HAISUGARCANE BG, trademark, used in Examples 2, 13 and 14;

1,3-Butylene glycol (1,3-BG): from Daicel Chemical Industries Limited, 1,3-butylene glycol, used in Examples 6 and 7 and Comparative Example 2;

Shea butter: from Kokyu Alcohol Kogyo Co., Ltd., Shea butter-RF, trademark;

Glycerin: from Kokyu Alcohol Kogyo Co., Ltd., TRIOL VE, trademark;

Ammonium acryloyldimethyltaurate NP copolymer: from Clariant, Aristoflex AVC, trademark;

Xanthan gum: from Sansho Co., Ltd., KELTROL T, trademark;

Carbomer, from Nikko Chemicals Co., Ltd., Carbopol ETD2050, trademark;

Dipentaerythrityl Hexahydroxystearate/Hexastearate/Hexarosinate: from Kokyu Alcohol Kogyo Co., Ltd., HAILUCENT 138DP, trademark;

Bis-ethoxydiglycol succinate: from Kokyu Alcohol Kogyo Co., Ltd., HAIAQUEOUSTER DCS, trademark;

Jojoba oil: from Kokyu Alcohol Kogyo Co., Ltd., ECOOIL RS, trademark;

Macadamia nut oil: from Nikko Chemicals Co., Ltd., NIKKOL Macadamian nut oil, trademark;

Stearyl alcohol: from Kokyu Alcohol Kogyo Co., Ltd., STEARYL ALCOHOL NX, trademark;

Stearyl trimonium chloride: from Clariant, Genamin STAC, trademark;

Distearyl dimonium chloride: from Clariant, Genamin DSAC, trademark;

Behen trimonium chloride: from Clariant, Genamin KDM-P, trademark;

Dicoco dimonium chloride: from Takemoto Oil & Fat Co., Ltd., Pionin B-2211, trademark;

Amodimethicone: from Dow Corning Toray Co., Ltd., SF 8452 C, trademark;

Cyclomethicone: from Dow Corning Toray Co., Ltd., SH245 Fluid, trademark;

Dimethicone: from GE Toshiba Silicone Co., Ltd., TSF451-100A, trademark, used in Examples 3 to 5;

Dimethicone: from Momentive Performance Materials Japan Co., Ltd., TSF45'-10A, trademark, used in Examples 6, 7 and 9 and Comparative Example 2;

Phenoxy ethanol: from Toho Chemical Industry Co., Ltd., Hisolve EPH, trademark;

Hydroxyethylcellulose: from Sumitomo Seika Chemicals Co., Ltd., HEC, trademark;

Hydroxypropyl methylcellulose: from Shin-Etsu Chemical Co., Ltd., Metolose 60SH-4000, trademark;

Polyquatanium-7: from Lion Corporation, Lipoflow-MN, trademark;

Silk hydrolysate: from Seiwa Kasei Co., Ltd., Promois silk-1000Q, trademark;

Highly polymerized methyl polysiloxane (1): from Dow Corning Toray Co., Ltd., BY 22-029, trademark.

Mica: from Merk & Co., Inc., Timiron Star Luster MP-1001, trademark;

$TiO_2$ coated mica: from Merk & Co., Inc., Timiron Star Luster MP-115, trademark;

Silicone treated barium sulfate: from Sakai Chemical Industry Co. Ltd., platy barium sulfate H series, trademark;

Boron nitride: from Mizushima Ferroalloy Co. Ltd., Boron Nitride SHP-6, trademark;

Spherical PMMA powder: from Sekisui Plastics Co., Ltd., MBX-8C, trademark;

Talc: from US Cosmetic Corporation, Soft Talc, trademark;

Nylon powder: from Dow Corning Toray Co., Ltd., Nylon powder-TR-1, trademark;

Silicone treated microparticles of titanium oxide: from TAYCA Corporation, SMT-100SAS, trademark;

Silicone treated microparticles of zinc oxide: from TAYCA Corporation, MZ-505S, trademark;

Silicone treated titanium oxide: from US Cosmetic Corporation, DHL-TRI-77891, trademark;

Silicone treated iron oxide yellow: from US Cosmetic Corporation, DHL-Y-77492, trademark;

Silicone treated iron oxide red: from US Cosmetic Corporation, DHL-R-77491, trademark;

Silicone treated iron oxide black: from US Cosmetic Corporation, DHL-B-77499, trademark;

Triethylhexanoin: from Kokyu Alcohol Kogyo Co., Ltd., TOG;

Neopentyl Glycol diisononanoate: from Kokyu Alcohol Kogyo Co., Ltd., NPDIN;

Ethylhexyl methoxycinnamate: from ISP Corporation, ESCALOL 557, trademark;

Tocopherol: from Eisai Co., Ltd., E-mix D, trademark;

Hexyldecyl isostearate: from Kokyu Alcohol Kogyo Co. Ltd., ICIS;

Neopentyl Glycol diethylhexanoate: from Kokyu Alcohol Kogyo Co., Ltd., KAK NDO, trademark;

Diglycerin/Dilinoleic Acid/Hydroxystearic Acid Copolymer: from Kokyu Alcohol Kogyo Co., Ltd., RISOCAST HSDA, trademark;

Sorbitan monoisostearate: from Nihon Emulsion Co., Ltd., EMALEX SPIS-100, trademark;

Dimethicone copolyol: from Evonik Goldschmidt GmbH, ABIL EM90, trademark;

Ethanol: from Amakasu Chemical Industries, Ethanol, trademark;

Dextrin palmitate: from Chiba Flour Milling Co., Ltd., Rheopearl KL2, trademark;

Microcrystalline wax: from Nikko Rica Corporation, purified microcrystalline wax;

Hydrophobicated titanium oxide: from US Cosmetic Corporation, NHS-TRI-77891, trademark;

Hydrophobicated iron oxide yellow: from US Cosmetic Corporation, NHS-Y-77492, trademark;

Hydrophobicated iron oxide red: from US Cosmetic Corporation, NHS-R-77491, trademark;

Hydrophobicated iron oxide black: from US Cosmetic Corporation, NHS-B-77499, trademark;

Nylon-6: from Ube Industries, Ltd., POMP605, trademark;

Crosslinked type silicone powder: from Dow Corning Toray Co., Ltd., Torefil E506C, trademark;

Mineral oil: from Kaneda Co., Ltd., HICALL K230, trademark;

Isostearyl isostearate: from Kokyu Alcohol Kogyo Co., Ltd., ISIS;

Isocetyl myristate: from Kokyu Alcohol Kogyo Co., Ltd., ICM-R, trademark;

Octyldodecyl neodecanoate: from Kokyu Alcohol Kogyo Co., Ltd., NEOLIGHT 2000, trademark;

Decamethylcyclopentanesiloxane: from Momentive Performance Materials Japan Co., Ltd., TSF405, trademark;

Hydrogenated castor oil dimer dilinoleate: from Kokyu Alcohol Kogyo Co., Ltd., RISOCAST DA-L, trademark;

Dextrin palmitate/ethylhexanoate: from Chiba Flour Milling Co., Ltd., Rheopearl TT2, trademark;

Candelilla wax: from STRAHL & PITSCH Inc., CANDELILLA WAX 75, trademark;

Carnauba wax: from STRAHL & PITSCH Inc., CARNAUBA WAX 142, trademark;

Beeswax: from Miki Chemical Industry & Co., Ltd., purified beeswax;

Polyethylene: from Baker Petrolite, Polywax 500, trademark;

Blue No. 1: from KISHI KASEI CO., LTD., Blue No. 1;

Diisostearyl malate: from Kokyu Alcohol Kogyo Co., Ltd., HAIMALATE DIS, trademark;

Glyceryl stearate (SE): from Nihon Emulsion Co., Ltd., EMALEX GMS-195, trademark;

Hydrophobicated ultramarine: from Whittaker Clark & Daniels Inc., 7104 Ultramarine Blue, trademark;

$TiO_2$ coated mica: from Merk & Co., Inc., Timiron Star Luster MP-115, trademark;

Hydrogenated polyisobutene: from NOF Corporation, PARLEAM18, trademark;

Polyglyceryl-2 diisostearate: from Kokyu Alcohol Kogyo Co., Ltd., RISOREX PGIS22, trademark;

Polyglyceryl-2 triisostearate: from Kokyu Alcohol Kogyo Co., Ltd., RISOREX PGIS23, trademark;

Pentaerythrityl tetraisostearate: from Kokyu Alcohol Kogyo Co., Ltd., KAK PTI, trademark;

Ethylhexyl hydroxystearate: from Kokyu Alcohol Kogyo Co. Ltd., RISOCAST IOHS, trademark;

Octyldodecyl stearoyl stearate: from Kokyu Alcohol Kogyo Co., Ltd., RISOCAST ODSHS, trademark;

Octyldodecanol: from Kokyu Alcohol Kogyo Co., Ltd., RISONOL 20SP, trademark;

Inulin stearate: from Chiba Flour Milling Co., Ltd., Rheopearl ISL2, trademark;

Glyceryl behenate/eicosanedioate: from The Nisshin OilIio Group, Ltd., NOMCORT HK-G, trademark;

Di(C20-40)alkyl dimer dilinoleate: from Koster Keunen Inc., Kester Wax K82-D, trademark;

Dibutyl lauroyl glutamide: from Ajinomoto Co., Inc., GP-1, trademark;

Stearyldimethicone: from Clariant, Silcare Silicone 41M65, trademark;

Amide terminated polyamide resin: from Arizona Chemical, Sylvaclear 200V, trademark;

Ester terminated polyamide resin: from Arizona Chemical, Uniclear 100VG, trademark;

Red No. 218: from KISHI KASEI CO., LTD., red No. 218;
Red No. 226: from KISHI KASEI CO., LTD., red No. 226;
Red No. 201: from KISHI KASEI CO., LTD., red No. 201;
Red No. 202: from KISHI KASEI CO., LTD., red No. 202;
Carmine: from Merk & Co., Inc., COLORONA CARMINE RED, trademark;

Titanium oxide: from Ishihara Sangyo Kaisha, Ltd., Tipaque CR-30, trademark;

Synthetic Fluorphlogopite, titanium oxide, iron oxide (lame luster): from Topy Industries, Ltd., Prominence RYH, trademark;

Borosilicic acid (Ca/Al), silica, titanium oxide, stannous oxide (lame luster): from Merk & Co., Inc., Ronastar Silver, trademark;

(PET/polymethylmethacrylate) laminate (lame luster): from Daiya Chemco, Ilidescent Glitter IF8101, trademark;

Trimethylolpropane triethylhexanoate: from Kokyu Alcohol Kogyo Co., Ltd., KAK TTO, trademark;

Isotridecyl isononanoate: from Kokyu Alcohol Kogyo Co., Ltd., KAK 139, trademark;

Hydrogenated castor oil isostearate, from Kokyu Alcohol Kogyo Co., Ltd., RISOCAST MIS, trademark;

Caprylic/Capric Triglyceride: from Kokyu Alcohol Kogyo Co., Ltd., TCG-M, trademark;

Isostearyl neopentanoate: from Kokyu Alcohol Kogyo Co., Ltd., NEOLIGHT 180P, trademark;

Neopentyl Glycol dicaprate: from Kokyu Alcohol Kogyo Co., Ltd., NPDC, trademark;

Ceresin: from STRAHL & PITSCH Inc., Ceresin SP1020, trademark;

Synthetic wax, Eethylene/propylene copolymer: from Nihon Natural Products, LIPWAX PZ80-20, trademark;

Yellow No. 4 Aluminum Lake: from KISHI KASEI CO., LTD., Yellow No. 4 Aluminum Lake;

Bengara: from US Cosmetic Corporation, NHS-R-77491, trademark;

Blue No. 1 Aluminum Lake: from KISHI KASEI CO., LTD., Blue No. 1 Aluminum Lake.

Storage stability, applicability (ease of spreading or sliminess), oily feeling, moisturizing ability, affinity with or adhesion to the skin, hair, eye lashes, eyelid and lips, safety to the skin and gloss-holding ability in each of the cosmetics prepared in the Examples and the Comparative Examples were determined as follows:

Storage Stability

Cosmetics, skin creams, hair treatments, foundations, mascaras, eye shadows, lip glosses and lipsticks, as indicated in the Examples and the Comparative Examples were prepared in accordance with the following predetermined process. Three samples were prepared per each Example. Then, two of the samples were stored in a temperature-controlled bath, one at 25 degrees C. and the other at 45 degrees C., for one month. Remaining one of the samples was maintained successively at −10 degrees C., 25 degrees C. and 45 degrees C., each for 8 hours and then successively at 45 degrees C., 25 degrees C. and −10 degrees C., each for 8 hours in a temperature-controlled room. It took 48 hours per one operation. This sequential operation was repeated 5 times. The samples thus obtained were observed in respect to deterioration of appearance (occurrence of bulky particles), coloration, smelliness and separation by organoleptic assessments. As a result, in all samples, no deterioration of appearance, no coloration and no smelliness were observed. Therefore, the evaluation of storage stability was carried out only with regard to separation. Each sample was observed visually. The indication of the evaluation results is as follows. When there was no separation in all samples, the cosmetic was rated as "G". When the sample at one of the temperatures showed separation even if it was slight, the cosmetic was rated as "M". When the samples at two or more of the temperatures showed separation, even if it was slight, the cosmetic was rated as "B".

Applicability (Ease of Spreading or Sliminess)

When each of the cosmetics obtained in the Examples and the Comparative Examples, skin creams, hair treatments, foundations, mascaras, eye shadows, lip glosses and lipsticks, was applied to the skin, "applicability" was evaluated by twenty panels. For skin creams, 0.5 g of each cosmetic was applied to the face. For hair treatments, 2.0 g were applied to the hair. For foundations, 1.0 g was applied to the face. For mascaras, 0.1 g was applied to the eye lashes. For eye shadows, 0.1 g was applied to the eyelids. For lip glosses and lipsticks, 0.2 g was applied to the lips. The indication of the evaluation results is as follows. When not less than 15 panels among 20 panels evaluated the cosmetic as "good applicability", it was rated as "G". When from 6 to 9 panels evaluated the cosmetic as "good applicability", it was rated as "M". When not more than five panels evaluated the cosmetic as "good applicability", it was rated as "B".

Oily Feeling and Moisturizing Ability

After each of the cosmetics obtained in the Examples and the Comparative Examples, skin creams, hair treatments, foundations, mascaras, eye shadows, lip glosses and lipsticks, was applied to the skin, "oily feeling and moisturizing ability" were evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "proper oily feeling and moisturizing ability", it was rated as "G". When from 6 to 9 panels evaluated the cosmetic as "proper oily feeling and moisturizing ability", it was rated as "M". When not more than five panels evaluated the cosmetic as "proper oily feeling and moisturizing ability", it was rated as "B".

Affinity with and Adhesion to the Skin Including Hair, Eye Lashes, Eyelids and Lips For each of the cosmetics obtained in the Examples and the Comparative Examples, skin creams, hair treatments, foundations, mascaras, eye shadows, lip glosses and lipsticks, "affinity with the skin and adhesion to the skin" were evaluated by twenty panels. For skin creams, 0.5 g of each cosmetic was applied to the face. For hair treatments, 2.0 g were applied to the hair. For foundations, 1.0 g was applied to the face. For mascaras, 0.1 g was applied to the eye lashes. For eye shadows, 0.1 g was applied to the eyelids. For lip glosses and lipsticks, 0.2 g was applied to the lips. The indication of the evaluation results is as follows. When not less than 15 panels among 20 panels evaluated the cosmetic as "good affinity with the skin and good adhesion to the skin after each cosmetic was applied", it was rated as "G". When from 6 to 9 panels evaluated the cosmetic as "good affinity with the skin and good adhesion to the skin after each cosmetic was applied", it was rated as "M". When not more than five panels evaluated the cosmetic as "good affinity with the skin and good adhesion to the skin after each cosmetic was applied", it was rated as "B".

Safety to the Skin

Subjects were twenty people, i.e. ten males and ten females. 0.05 g of each cosmetic obtained in the Examples or the Comparative Examples was applied to a circular patch with cotton lint of 1.0 cm diameter, which patch was applied to the foream flexor of each subject and left for 24 hours. The patch was removed and the skin was examined 1 hour later and 24 hours later to rate the skin conditions of each subject according to the following criteria. When the results 1 hour later and 24 hours later were different, the stronger response was used for rating. When the 20 subjects exhibited (−), the rating was "G", when 1 to 2 subjects exhibited (+−) and the other subjects exhibited (−), the rating was "M"; and when three or more subjects exhibited (+−) and the other subjects exhibited (−) or when one or more subjects exhibited (+) to (+++), the rating was "B". For a hair treatment, aqueous 0.5% solution was used.

| Rating Criteria | |
|---|---|
| Skin Conditions | Rating |
| Erythema, edema, and blister | (+++) |
| Erythema and edema | (++) |
| Erythema | (+) |
| Slight erythema | (+−) |
| No erythema and no edema | (−) |

Gloss-Holding Effect

After each of the cosmetics obtained in the Examples and the Comparative Examples, lip glosses and lipsticks, was applied to the lips, "gloss-holding effect" was evaluated as follows: Twenty panels were used and 0.2 g of each cosmetic was applied to the lips. When the cosmetic was contacted with saliva, the degree of muddy appearance of the lips was estimated visually. The indication of the evaluation results is as follows. When not less than 15 panels among 20 panels evaluated the cosmetic as "significant gloss-holding effect", it was rated as "G". When from 6 to 9 panels evaluated the cosmetic as "significant gloss-holding effect", it was rated as "M". When not less than five panels evaluated the cosmetic as "significant gloss-holding effect", it was rated as "B".

Examples 1 and 2

Skin Cream

Each of the compositions (A) and (B) indicated in Table 2 was separately dissolved homogenously at a temperature of 75 to 80 degrees C. Next, Composition (B) was added to Composition (A) under stirring and then emulsified with a homomixer. The mixture thus obtained was then cooled to 30 degrees C. under stirring to prepare a skin cream.

Comparative Example 1

The procedures of Example 1 were repeated, except that the ester compound obtained in Comparative Preparation Example 3 was used in place of the ester compound obtained in Preparation Example 2.

The results in Examples 1 and 2, and Comparative Example 1 are shown in Table 2. Units of all figures indicated in Table 2 and in the following tables, Tables 3 to 10, are % by mass.

TABLE 2

| | Ingredient | Ex. 1 | Ex. 2 | Com. Ex. 1 |
|---|---|---|---|---|
| (A) | Ester compound obtained in Prep. Ex. 2 | 2.00 | — | — |
| | Ester compound obtained in Prep. Ex. 4 | — | 6.00 | — |
| | Ester compound obtained in Com. Prep. Ex. 3 | — | — | 2.00 |
| | Squalane | 8.00 | 7.00 | 8.00 |
| | Polyglceryl-2 isostearate/dimer dilinoleate copolymer | 2.00 | — | 2.00 |
| | Polyglyceryl-10 stearate | 1.50 | — | 1.50 |
| | Polysorbate-80 | — | 1.50 | — |
| | Hydrogenated lecithin | — | 0.50 | — |
| | Behenyl alcohol | 1.00 | — | 1.00 |

TABLE 2-continued

| | Ingredient | Ex. 1 | Ex. 2 | Com. Ex. 1 |
|---|---|---|---|---|
| | Hydrogenated rapeseed alcohol | — | 3.00 | — |
| | Cetearyl alcohol | 2.00 | — | 2.00 |
| | Pentylene glycol | 3.00 | — | 3.00 |
| | Paraffin | — | 0.50 | — |
| | Dipropylene glycol | 3.00 | — | 3.00 |
| | 1,3-Butylene glycol | — | 1.00 | — |
| | Shea butter | 2.00 | 4.00 | 2.00 |
| (B) | Glycerin | 5.00 | 3.00 | 5.00 |
| | Ammonium acryloyldimethyltaurate/VP copolymer | 0.25 | — | 0.25 |
| | Xanthan gum | 0.10 | 0.20 | 0.10 |
| | Carbomer | — | 0.20 | — |
| | Sodium hydroxide | — | 0.05 | — |
| | Water | 70.15 | 73.05 | 70.15 |
| Total | | 100.00 | 100.00 | 100.00 |
| Evaluation result | Storage stability | G | G | G |
| | Applicability(ease of spreading or sliminess) | G | G | M |
| | Oily feeling and moisturizing ability | G | G | M |
| | Affinity with the skin and adhesion to the skin | G | G | B |
| | Safety to the skin | G | G | G |

In Examples 1 and 2, skin creams were prepared using the ester compounds obtained in Preparation Examples 2 and 4, respectively. All the cosmetics exhibited good properties regardless of the kind of fatty acid used in the preparation of the ester compound. Meanwhile, in Comparative Example 1, the ester compound obtained in Preparation Example 2 used in Example 1 was changed to the ester compound obtained in Comparative Preparation Example 3, that is, the ester compound which was obtained using isostearic acid having 18 carbon atoms as a fatty acid. The number of carbon atom of the fatty acid from which the ester compound was made was beyond the upper limit of the present invention. As a result, the cosmetic exhibited somewhat lowered applicability and oily feeling and moisturizing ability, and poor affinity with the skin and poor adhesion to the skin.

Examples 3 to 6

Hair Treatment

Each of the compositions (A) and (B) indicated in Table 3 was separately dissolved homogenously at a temperature of 75 to 80 degrees C. Next, Composition (B) was added to Composition (A) under stirring and then emulsified with a homomixer. Then, Component (C) was added to the emulsified product under stirring to obtain a mixture. The mixture thus obtained was then cooled to 30 degrees C. under further stirring to prepare a hair treatment. The evaluation results are shown in Table 3.

TABLE 3

| | Ingredient | Ex. 3 | Ex. 4 | Ex. 5 | Ex. 6 |
|---|---|---|---|---|---|
| (A) | Ester compound obtained in Prep. Ex. 1 | 3.50 | — | 2.80 | 2.80 |
| | Ester compound obtained in Prep. Ex. 2 | — | 6.00 | — | — |
| | Ester compound obtained in Prep. Ex. 6 | — | — | 2.00 | — |
| | Ester compound obtained in Prep. Ex. 8 | — | — | — | 2.00 |
| | Dipentaerythrityl Hexahydroxystearate/Hexastearate/Hexarosinate | 2.00 | — | — | — |
| | Polyglyceryl-2 isostearate/dimer dilinoleate copolymer | — | 1.00 | — | — |
| | Bis-ethoxydiglycol succinate | 3.00 | — | — | — |
| | Jojoba oil | 1.00 | — | — | — |
| | Macadamia nut oil | — | 1.00 | — | — |
| | Stearyl alcohol | 9.00 | — | 6.00 | 6.00 |
| | Cetearyl alcohol | — | 9.00 | — | — |
| | Behenyl alcoliol | — | — | 2.00 | 2.00 |
| | Dipropylene glycol | 4.00 | 3.00 | 3.00 | 3.00 |
| | Stearyl trimonium chloride | 1.00 | — | 1.00 | 1.00 |
| | Distearyl dimonium chloride | — | 1.00 | 1.00 | 1.00 |
| | Behen trimonium chloride | — | 0.50 | — | — |
| | Dicoco dimoniom chloride | — | 1.00 | — | — |
| | Amodimethicone | 0.50 | — | 0.20 | 0.20 |
| | Cyclomethicone | — | 1.00 | — | — |
| | Dimethicone | 1.00 | 2.00 | 3.00 | 3.00 |
| | Phenoxy ethanol | — | 0.10 | — | — |
| (B) | Hydroxyethyl cellulose | 0.30 | — | 0.30 | 0.30 |
| | Hydroxypropyl methylcellulose | — | 0.20 | — | — |
| | Ammonium acryloyldimethyltaurate/VP copolymer | — | 0.20 | — | — |
| | Pentylene glycol | 3.00 | — | — | — |
| | Polyquatanium-7 | — | 1.00 | — | — |
| | Silk hydrolysate | — | — | 0.02 | 0.02 |
| | Glycolic acid | 1.00 | — | 1.00 | 1.00 |

TABLE 3-continued

| | Ingredient | Ex. 3 | Ex. 4 | Ex. 5 | Ex. 6 |
|---|---|---|---|---|---|
| | Methylparaben | — | — | 0.20 | 0.20 |
| | Purified water | 69.29 | 74.00 | 76.48 | 76.48 |
| (C) | Highly polymerized methyl polysiloxane (1) | 1.40 | — | 1.00 | 1.00 |
| Total | | 100.00 | 101.00 | 100.00 | 100.00 |
| Evaluation result | Storage stability | G | G | G | G |
| | Applicability (ease of spreading or sliminess) | G | G | G | G |
| | Oily feeling and moisturizing ability | G | G | G | G |
| | Affinity with the skin and adhesion to the skin | G | G | G | G |
| | Safety to the skin | G | G | G | G |

In Examples 3 and 4, hair treatments were prepared using the ester compounds obtained in Preparation Examples 1 and 2, respectively. Either cosmetic exhibited good properties regardless of the molar ratio of an isononanoic acid residue comprised in the ester compound. And in Example 5, a hair treatment was prepared using the ester compound obtained in Preparation Example 1 and the ester compound obtained in Preparation Example 6. In Example 6, a hair treatment was prepared using the ester compound obtained in Preparation Example 1 and the ester compound obtained in Preparation Example 8. It was found that the hair treatment obtained using a mixture of the ester compounds which were made from different fatty acids also exhibited good properties.

Examples 7 and 8

Compact Powder Foundation

Ingredients of the composition (A) indicated in Table 4 were homogeneously dispersed with a Henschel mixer. Separately, ingredients of the composition (B) were heated to 60 degrees C. and mixed homogeneously and dissolved. Next, Composition (B) was added to Composition (A) under stirring with a Henschel mixer to disperse homogenously. After the mixture thus obtained was cooled to 30 degrees C. and ground, it was packed into a gold plate and then was compact molded to prepare a compact powder foundation.

Comparative Example 2

Compact Powder Foundation

The procedures of Example 8 were repeated, except that the ester compound obtained in Comparative Preparation Example 2 was used in place of the ester compound obtained in Preparation Example 3.

The results in Examples 7 and 8 and Comparative Example 2 are shown in Table 4.

TABLE 4

| | Ingredient | Ex. 7 | Ex. 8 | Com. Ex. 2 |
|---|---|---|---|---|
| (A) | Mica | 24.00 | 21.00 | 21.00 |
| | TiO₂ coated mica | 10.00 | 11.00 | 11.00 |
| | Silicone treated barium sulfate | 7.00 | 8.10 | 8.10 |
| | Boron nitride | 2.40 | 3.00 | 3.00 |
| | Spherical PMMA powder | 5.00 | 4.00 | 4.00 |
| | Talc | 17.40 | 16.00 | 16.00 |
| | Nylon powder | 3.70 | 4.00 | 4.00 |
| | Silicone treated microparticles of titanium oxide | 5.20 | 4.00 | 4.00 |
| | Silicone treated microparticles of zinc oxide | 3.20 | 4.00 | 4.00 |
| | Silicone treated titanium oxide | 8.00 | 9.00 | 9.00 |
| | Silicone treated iron oxide yellow | 1.50 | 2.50 | 2.50 |
| | Silicone treated iron oxide red | 0.40 | 0.60 | 0.60 |
| | Silicone treated iron oxide black | 0.20 | 0.15 | 0.15 |
| (B) | Ester compound obtained in Prep. Ex. 1 | 1.00 | — | — |
| | Ester compound obtained in Prep. Ex. 3 | — | 2.00 | — |
| | Ester compound obtained in Com. Prep. Ex. 2 | — | — | 2.00 |
| | Dimethicone | 3.00 | 2.00 | 2.00 |
| | Squalane | 1.50 | — | — |
| | Triethylhexanoin | 2.00 | — | — |
| | Neopentyl glycol diisononanoate | — | 2.00 | 2.00 |
| | Ethylhexyl methoxycinnamate | — | 3.00 | 3.00 |
| | 1,3-Butylene glycol | 4.50 | 3.00 | 3.00 |
| | Phenoxy ethanol | — | 0.60 | 0.60 |
| | Tocopherol | — | 0.05 | 0.05 |
| Total | | 100.00 | 100.00 | 100.00 |
| Evaluation result | Storage stability | G | G | M |
| | Applicability (ease of spreading or sliminess) | G | G | M |
| | Oily feeling and moisturizing ability | G | G | M |
| | Affinity with the skin and adhesion to the skin | G | G | B |
| | Safety to the skin | G | G | B |

In Examples 7 and 8, compact powder foundations were prepared using the ester compounds obtained in Preparation Examples 1 and 3, respectively. Either cosmetic exhibited good properties regardless of the molar ratio of an isononanoic acid residue comprised in the ester compound. Meanwhile, in Comparative Example 2, the ester compound obtained in Preparation Example 3 used in Example 8 was changed to the ester compound obtained in Comparative Preparation Example 2, that is, the ester compound which was obtained using isobutanoic acid, isobutyric acid, having 4 carbon atoms as a fatty acid. The carbon number of the fatty acid from which the ester compound was made was below the lower limit of the present invention. As a result, the cosmetic exhibited somewhat lowered storage stability, applicability and oily feeling and moisturizing ability, and poor affinity with the skin and poor adhesion to the skin and poor safety to the skin.

Examples 9 to 11

W/O Type Creamy Foundation

Each of the compositions (A) and (B) indicated in Table 5 was separately dissolved homogenously at a temperature of 75 to 80 degrees C. Next, Composition (B) was added to Composition (A) under stirring and then emulsified with a homomixer. The mixture thus obtained was then cooled to 30 degrees C. under stirring to prepare a creamy foundation.

Comparative Example 3

W/O Type Creamy Foundation

The procedures of Example 11 were repeated, except that the ester compound obtained in Comparative Preparation Example 3 was used in place of the ester compound obtained in Preparation Example 5.

The results in Examples 9 to 11, and Comparative Example 3 are shown in Table 5.

TABLE 5

| | Ingredient | Ex. 9 | Ex. 10 | Ex. 11 | Com. Ex. 3 |
|---|---|---|---|---|---|
| (A) | Ester compound obtained in Prep. Ex. 2 | 5.00 | — | — | — |
| | Ester compound obtained in Prep. Ex. 4 | — | 2.50 | — | — |
| | Ester compound obtained in Prep. Ex. 5 | — | — | 16.50 | — |
| | Ester compound obtained in Com. Prep. Ex. 3 | — | — | — | 16.50 |
| | Hexyldecyl isostearate | 16.00 | — | — | — |
| | Neopentyl glycol diethylhexanoate | — | 3.00 | 5.00 | 5.00 |
| | Squalane | 5.00 | — | 2.00 | 2.00 |
| | Cyclomethicone | — | 20.00 | 5.00 | 5.00 |
| | Dimethicone | — | 2.00 | — | — |
| | Diglycerin/Dilinoleic Acid/Hydroxystearic Acid | — | — | 1.50 | 1.50 |
| | Sorbitan monoisostearate | 1.00 | — | 1.00 | 1.00 |
| | Dimethicone copolyol | — | 1.20 | — | — |
| | Dipropylene glycol | 3.00 | — | 5.00 | 5.00 |
| | Pentylene glycol | 2.00 | 2.00 | — | — |
| | Ethanol | 2.00 | 2.00 | — | — |
| | Cetostearyl alcohol | — | 1.00 | — | — |
| | Hydrogenated rapeseed alcohol | — | 0.50 | — | — |
| | Dextrin palmitate | 3.00 | 2.00 | 3.00 | 3.00 |
| | Microcrystalline wax | — | 4.00 | 3.00 | 3.00 |
| | Hydrophobicated titanium oxide | 8.00 | 7.00 | 7.50 | 7.50 |
| | Hydrophobicated iron oxide yellow | 1.20 | 1.20 | 1.25 | 1.25 |
| | Hydrophobicated iron oxide red | 0.30 | 0.30 | 0.28 | 0.28 |
| | Hydrophobicated iron oxide black | 0.15 | 0.15 | 0.18 | 0.18 |
| | Talc | 1.40 | 1.35 | 2.00 | 2.00 |
| | Ethylhexyl methoxycinnamate | 1.00 | 1.00 | 1.00 | 1.00 |
| | Nylon-6 | 0.50 | — | 0.20 | 0.20 |
| | Crosslinked type silicone powder | — | 2.00 | 1.00 | 1.00 |
| (B) | Glyrcerin | 2.00 | 3.00 | 2.00 | 2.00 |
| | Hydroxyethylcellulose | — | 0.30 | — | — |
| | Carbomer | — | — | 0.40 | 0.40 |
| | Sodium hydroxide | — | — | 0.15 | 0.15 |
| | Preservative | proper amount | proper amount | proper amount | proper amount |
| | Purified water | 48.46 | 43.50 | 42.04 | 42.04 |
| Total | | 100.00 | 100.00 | 100.00 | 100.00 |
| Evaluation result | Stotage stability | G | G | G | G |
| | Applicability (ease of spreading or sliminess) | G | G | G | M |
| | Oily feeling and moisturizing ability | G | G | G | M |
| | Affinity with the skin and adhesion to the skin | G | G | G | B |
| | Safety to the skin | G | G | G | G |

In Examples 9, 10 and 11, creamy foundations were prepared using the ester compounds obtained in Preparation Examples 2, 4 and 5, respectively. All the cosmetics exhibited good properties regardless of the kind of fatty acid used in the preparation of the ester compound. Meanwhile, in Comparative Example 3, the ester compound obtained in Preparation Example 5 used in Example 11 was changed to the ester compound obtained in Comparative Preparation Example 3, that is, the ester compound which was obtained using isostearic acid having 18 carbon atoms as a fatty acid. Also in creamy foundations, when the carbon number of the fatty acid from which the ester compound was made was beyond the upper limit of the present invention, the cosmetic exhibited somewhat lowered applicability and oily feeling and moisturizing ability, and poor affinity with the skin and poor adhesion to the skin.

Examples 12 to 14

Mascara

All the ingredients other than those in a form of fine particles, indicated in Table 6 were dissolved homogenously at 100 degrees C. to obtain a mixture, to which the aforesaid ingredients in a form of fine particles were then added to make a dispersion. Next, the dispersion was cooled to room temperature under stirring to prepare a mascara.

The results in Examples 12 to 14 are shown in Table 6.

TABLE 6

| | Ingredient | Ex. 12 | Ex. 13 | Ex. 14 |
|---|---|---|---|---|
| | Ester compound obtained in Prep. Ex. 1 | 9.00 | — | — |
| | Ester compound obtained in Prep. Ex. 6 | — | 27.00 | — |
| | Ester compound obtained in Prep. Ex. 8 | — | — | 27.00 |
| | Neopentyl glycol diisononanoate | 40.00 | 5.00 | 5.00 |
| | Mineral oil | 11.00 | 15.00 | 15.00 |
| | Neopentyl glycol diethylhexanoate | — | 4.90 | 4.90 |
| | Isostearyl isostearate | 2.00 | — | — |
| | Isocetyl myristate | 1.00 | — | — |
| | Octyldodecyl neodecanoate | 4.40 | — | — |
| | Decamethylcyclopentanesiloxane | — | 10.00 | 10.00 |
| | Polyglyceryl-2 isostearate/dimer dilinoleate copolymer | — | 2.00 | 2.00 |
| | Hydrogenated castor oil dimer dilinoleate | — | 1.00 | 1.00 |
| | Dextrin palmitate | 5.00 | — | — |
| | Dextrin palmitate/ethylhexanoate | — | 10.00 | 10.00 |
| | Candelilla wax | 8.00 | — | — |
| | Carnauba wax | — | 3.00 | 3.00 |
| | Beeswax | — | 1.00 | 1.00 |
| | Microcrystalline wax | 3.00 | — | — |
| | Polyethylene | 4.00 | 8.00 | 8.00 |
| | Hydrophobicated iron oxide black | 10.50 | 10.50 | 10.50 |
| | Hydrophobicated iron oxide red | — | 0.50 | 0.50 |
| | Blue No. 1 | 2.00 | 2.00 | 2.00 |
| | Perfume | proper amount | proper amount | proper amount |
| | Tocopherol | 0.10 | 0.10 | 0.10 |
| Total | | 100.00 | 100.00 | 100.00 |
| Evaluation result | Storage stability | G | G | G |
| | Applicability (ease of spreading or sliminess) | G | G | G |
| | Oily feeling and moisturizing ability | G | G | G |
| | Affinity with the skin and adhesion to the skin | G | G | G |
| | Safety to the skin | G | G | G |

In Examples 12, 13 and 14, mascaras were prepared using the ester compounds obtained in Preparation Examples 1, 6 and 8, respectively. All the cosmetics exhibited good properties regardless of the kind of fatty acid used in the preparation of the ester compound.

Examples 15 to 17

Eye Shadow

Each of the compositions (A) and (B) indicated in Table 7 was separately dissolved homogenously at a temperature of 75 to 80 degrees C. Next, Composition (B) was added to Composition (A) under stirring and then emulsified with a homomixer. The mixture thus obtained was then cooled to 30 degrees C. under stirring to prepare an eye shadow.

The results in Examples 15 to 17 are shown in Table 7.

TABLE 7

| | Ingredient | Ex. 15 | Ex. 16 | Ex. 17 |
|---|---|---|---|---|
| (A) | Ester compound obtained in Prep. Ex. 3 | 4.00 | — | — |
| | Ester compound obtained in Prep. Ex. 5 | — | 5.00 | — |
| | Ester compound obtained in Prep. Ex. 7 | — | — | 5.00 |
| | Hydrogenated castor oil dimer dilinoleate | 1.00 | 2.00 | 2.00 |
| | Neopentyl glycol diethylhexanoate | 2.00 | — | — |
| | Isostearyl isostearate | — | 0.50 | 0.50 |
| | Triethylhexanoin | — | 0.50 | 0.50 |
| | Mineral oil | 1.00 | — | — |
| | Diisostearyl malate | 5.00 | — | — |
| | Glyceryl stearate(SE) | 1.50 | — | — |
| | Polyglyceryl-10 stearate | 1.00 | — | — |
| | Sorbitan monoisostearate | — | 1.00 | 1.00 |

TABLE 7-continued

|  | Ingredient | Ex. 15 | Ex. 16 | Ex. 17 |
|---|---|---|---|---|
|  | Dextrin palmitate | 3.00 | 3.00 | 3.00 |
|  | Hydrophobicated ultramarine | 8.20 | 8.20 | 8.20 |
|  | Hydrophobicated iron oxide black | 1.10 | 1.10 | 1.10 |
|  | $TiO_2$ coated mica | 1.00 | 1.00 | 1.00 |
|  | Cyclomethicone | 9.50 | 11.00 | 11.00 |
| (B) | Glycerin | 2.00 | 1.50 | 1.50 |
|  | 1,3-Butylene glycol | 2.00 | 1.50 | 1.50 |
|  | Pentylene glycol | 3.00 | 3.00 | 3.00 |
|  | Preservative | proper amount | proper amount | proper amount |
|  | Purified water | 54.70 | 60.70 | 60.70 |
| Total |  | 100.00 | 100.00 | 100.00 |
| Evaluation result | Storage stability | G | G | G |
|  | Applicability (ease of spreading or sliminess) | G | G | G |
|  | Oily feeling and moisturizing ability | G | G | G |
|  | Affinity with the skin and adhesion to the skin | G | G | G |
|  | Safety to the skin | G | G | G |

In Examples 15, 16 and 17, eye shadows were prepared using the ester compounds obtained in Preparation Examples 3, 5 and 7, respectively. All the cosmetics exhibited good properties regardless of the kind of fatty acid used in the preparation of the ester compound.

Examples 18 to 21

Pasty Lip Gloss

Ingredients indicated in Table 8 were dissolved homogenously at 110 degrees C., and then deaerate. Next, the mixture thus obtained was cooled to 30 degrees C. to prepare a lip gloss.

Comparative Examples 4

Pasty Lip Gloss

The procedures of Example 19 were repeated, except that the ester compound obtained in Comparative Preparation Examples 3 was used in place of the ester compound obtained in Preparation Example 2.

The results in Examples 18 to 21, and Comparative Example 4 are shown in Table 8.

TABLE 8

| Ingredient | Ex. 18 | Ex. 19 | Ex. 20 | Ex. 21 | Com. Ex. 4 |
|---|---|---|---|---|---|
| Ester compound obtained in Prep. Ex. 2 | 30.00 | 40.00 | 10.00 | — | — |
| Ester compound obtained in Prep. Ex. 8 | — | — | — | 10.00 | — |
| Ester compound obtained in Com. Prep. Ex. 3 | — | — | — | — | 40.00 |
| Hydrogenated polyisobutene | — | 35.00 | 15.00 | — | 35.00 |
| Hydrogenated castor oil dimer dilinoleate | — | — | — | 2.00 | — |
| Polyglyceryl-2 isostearate/dimer dilinoleate copolymer | 40.00 | — | 25.00 | 38.00 | — |
| Diglycerin/Dilinoleic Acid/Hydroxystearic Acid Copolymer | — | — | 2.00 | — | — |
| Polyglyceryl-2 diisostearate | 10.00 | — | 10.00 | — | — |
| Polyglyceryl-2 triisostearate | — | 7.00 | 5.00 | 5.00 | 7.00 |
| Diisostearyl malate | 8.00 | 4.02 | 15.00 | 5.00 | 4.02 |
| Pentaerythrityl tetraisostearate | 4.50 | — | 10.00 | 8.40 | — |
| Ethylhexyl hydroxystearate | 1.70 | 3.00 | — | 15.00 | 3.00 |
| Octyldodecyl stearoyl stearate | — | 3.00 | 6.80 | — | 3.00 |
| Squalane | — | 2.00 | — | — | 2.00 |
| Jojoba oil | — | 2.00 | — | — | 2.00 |
| Octyldodecanol | — | — | — | 10.00 | — |
| Dextrin palmitate/ethylhexanoate | 3.50 | 2.00 | — | — | 2.00 |
| Inulin stearate | — | — | — | 2.00 | — |
| Glyceryl behenate/eicosanedioate | — | — | — | 2.00 | — |
| Di(C20-40)alkyl dimer-dilinoleate | 1.00 | — | — | — | — |
| Dibutyllauroylglutamide | — | — | 0.50 | — | — |
| Stearyldimethicone | — | 1.50 | — | — | 1.50 |
| Amide terminated polyamide resin | — | — | — | 0.50 | — |
| Ester terminated polyamide resin | — | — | — | 0.80 | — |
| Red No. 218 | — | — | — | 0.30 | — |
| Red No. 226 | 0.30 | — | — | — | — |
| Red No. 201 | — | 0.01 | — | — | 0.01 |
| Red No. 202 | — | 0.02 | — | — | 0.02 |
| Carmine | — | — | 0.30 | — | — |
| Titanium oxide | — | 0.15 | — | — | 0.15 |
| TiO2 coated mica (pearlescent agent) | 1.00 | — | — | 0.50 | — |
| Synthetic Fluorophogopite, titanium oxide, iron oxide (lame luster) | — | 0.30 | — | — | 0.30 |

TABLE 8-continued

| Ingredient | | Ex. 18 | Ex. 19 | Ex. 20 | Ex. 21 | Com. Ex. 4 |
|---|---|---|---|---|---|---|
| | Borosilicic acid(Ca/Al), silica, titanium oxide, stannous oxide (lame luster) | — | — | 0.40 | — | — |
| | (PET/polymethylmethacrylate) laminate (lame luster) | — | — | — | 0.50 | — |
| Total | | 100.00 | 100.00 | 100.00 | 100.00 | 100.00 |
| Evaluation result | Storage stability | G | G | G | G | G |
| | Applicability (ease of spreading or sliminess) | G | G | G | G | M |
| | Oily feeling and moisturizing ability | G | G | G | G | G |
| | Affinity with the skin and adhesion to the skin | G | G | G | G | B |
| | Gloss after application | G | G | G | G | G |
| | Gloss-holding effect | G | G | G | G | B |
| | Safety to the skin | G | G | G | G | G |

In all the Examples 18 to 20, pasty lip glosses were prepared using the ester compound obtained in Preparation Example 2. All the cosmetics exhibited good properties regardless of the amount of the ester compound and the kind of other ingredients blended. And in Example 21, a pasty lip gloss was prepared using the ester compound obtained in Preparation Example 8. The cosmetic exhibited good properties. Meanwhile, in Comparative Example 4, the ester compound obtained in Preparation Example 2 used in Example 19 was changed to the ester compound obtained in Comparative Preparation Example 3, that is, the ester compound which was obtained using isostearic acid having 18 carbon atoms as a fatty acid. The applicability was somewhat lowered and the affinity with the skin and the adhesion to the skin were poor. As shown in Table8, the ester compound obtained in Comparative Preparation Example 3, which was prepared using isostearic acid, exhibited poor gloss upon contact with water. Therefore, a pasty lip gloss using said ester compound also exhibited poor gloss-holding effect.

Examples 22 and 23

Palette Type Lip Gloss

Ingredients indicated in Table 9 were dissolved homogenously at 110 degrees C., and then deaerate. Next, the mixture thus obtained was poured into a proper mold and cooled to 30 degrees C. to prepare a lip gloss.

Comparative Examples 5

Palette Type Lip Gloss

The procedures of Example 22 were repeated, except that the ester compound obtained in Comparative Preparation Examples 3 was used in place of the ester compound obtained in Preparation Example 2.

The results in Examples 22 and 23 and Comparative Example 5 are shown in Table 9.

TABLE 9

| Ingredient | Ex. 22 | Ex. 23 | Com. Ex. 5 |
|---|---|---|---|
| Ester compound obtained in Prep. Ex. 2 | 25.00 | — | — |
| Ester compound obtained in Prep. Ex. 1 | — | 9.00 | — |
| Ester compound obtained in Com. Prep. Ex. 3 | — | — | 25.00 |
| Hydrogenated polyisobutene | 20.00 | — | 20.00 |
| Hydrogenated castor oil dimer dilinoleate | — | 5.00 | — |
| Diglycerin/Dilinoleic Acid/Hydroxystearic Acid Copolymer | — | 1.00 | — |
| Polyglyceryl-2 isostearate/dimer dilinoleate copolymer | 10.00 | 30.00 | 10.00 |
| Polyglyceryl-2 diisostearate | 20.00 | 15.00 | 20.00 |
| Polyglyceryl-2 triisostearate | — | 15.00 | — |
| Diisostearyl malate | 5.00 | 10.84 | 5.00 |
| Pentaerythrityl tetraisostearate | 5.00 | — | 5.00 |
| Trimethylolpropane triethylhexanoate | — | 1.00 | — |
| Ethylhexyl hydroxystearate | — | 1.00 | — |
| Isotridecyl isononanoate | — | 4.00 | — |
| Octyldodecyl stearoyl stearate | 9.25 | — | 9.25 |
| Squalane | — | 1.00 | — |
| Jojoba oil | — | 1.00 | — |
| Octyldodecanol | — | 1.00 | — |
| Dextrin palmitate/ethylhexanoate | — | 1.50 | — |
| Inulin stearate | — | 1.00 | — |
| Dibutyllauroylglutamide | — | 1.50 | — |
| Amide terminated polyamide resin | 2.00 | — | 2.00 |
| Ester terminated polyamide resin | 3.00 | — | 3.00 |
| Red No. 218 | 0.10 | — | 0.10 |
| Red No. 226 | 0.20 | — | 0.20 |
| Red No. 201 | — | 0.02 | — |
| Red No. 202 | — | 0.01 | — |
| Carmine | 0.05 | — | 0.05 |
| Titanium oxide | — | 0.13 | — |
| TiO$_2$ coated mica (pearlescent agent) | — | 1.00 | — |
| Synthetic Fluorphlogopite, titanium oxide, iron oxide (lame luster) | 0.10 | — | 0.10 |

TABLE 9-continued

| Ingredient | Ex. 22 | Ex. 23 | Com. Ex. 5 |
|---|---|---|---|
| Borosilicic acid(Ca/Al), silica, titanium oxide, stannous oxide (lame luster) | 0.10 | — | 0.10 |
| (PET/polymethylmethacrylate) laminate (lame luster) | 0.20 | — | 0.20 |
| Total | 100.00 | 100.00 | 100.00 |
| Evaluation result — Storage stability | G | G | G |
| Applicability (ease of spreading or sliminess) | G | G | M |
| Oily feeling and moisturizing ability | G | G | G |
| Affinity with the skin and adhesion to the skin | G | G | B |
| Gloss after application | G | G | G |
| Gloss-holding effect | G | G | B |
| Safety to the skin | G | G | G |

In Examples 22 and 23, palette type lip glosses were prepared using the ester compounds obtained in Preparation Examples 2 and 1, respectively. Although intrinsic glosses of these ester compounds were somewhat different from each other, both lip glosses made from these ester compounds exhibited good properties, which were not different from each other. Meanwhile, in Comparative Example 5, the ester compound obtained in Preparation Example 2 used in Example 22 was changed to the ester compound obtained in Comparative Preparation Example 3, that is, the ester compound which was obtained using isostearic acid having 18 carbon atoms as a fatty acid. The applicability was somewhat lowered and the affinity with the skin and the adhesion to the skin were poor. The gloss-holding effect was also poor due to the poor properties of the ester compound obtained using isostearic acid, as described in Comparative Example 4.

Examples 24 to 27

Lipstick

Ingredients indicated in Table 10 were dissolved homogenously at 110 degrees C., and then deaerate. Next, the mixture thus obtained was poured into a proper mold and cooled at 10 degrees C. for 20 minutes to prepare a lipstick.

Comparative Example 6

Lipstick

The procedures of Example 27 were repeated, except that the ester compound obtained in Comparative Preparation Example 3 was used in place of the ester compound obtained in Preparation Example 5.

The results in Examples 24 to 27, and Comparative Example 6 are shown in Table 10.

TABLE 10

| Ingredient | Ex. 24 | Ex. 25 | Ex. 26 | Ex. 27 | Com. Ex. 6 |
|---|---|---|---|---|---|
| Ester compound obtained in Prep. Ex. 2 | 10.00 | — | 33.00 | — | — |
| Ester compound obtained in Prep. Ex. 5 | — | 15.00 | — | 22.24 | — |
| Ester compound obtained in Com. Prep. Ex. 3 | — | — | — | — | 22.24 |
| Hydrogenated polyisobutene | 5.00 | — | — | — | — |
| Hydrogenated castor oil dimer dilinoleate | 20.00 | — | — | 14.00 | 14.00 |
| Diglycerin/Dilinoleic Acid/Hydroxystearic Acid Copolymer | — | 6.00 | — | — | — |
| Polyglyceryl-2 isostearate/dimer dilinoleate copolymer | — | — | 5.00 | 4.00 | 4.00 |
| Dipentaerythrityl Hexahydroxystearate/Hexastearate/Hexarosinate | — | 11.00 | 10.00 | — | — |
| Hydrogenated castor oil isostearate | — | — | 6.00 | — | — |
| Polyglyceryl-2 diisostearate | — | 5.00 | 5.00 | — | — |
| Polyglyceryl-2 triisostearate | 5.00 | — | 9.00 | 5.00 | 5.00 |
| Diisostearyl malate | 10.00 | 14.00 | — | 9.00 | 9.00 |
| Pentaerythrityl tetraisostearate | — | 8.00 | — | 9.00 | 9.00 |
| Caprylic/Capric Triglyceride | 15.00 | 14.30 | 8.70 | 18.00 | 18.00 |
| Ethylhexyl hydroxystearate | — | 9.60 | 2.00 | — | — |
| Isostearyl neopentanoate | 4.00 | — | 2.00 | — | — |
| Neopentyl glycol dicaprate | 2.00 | — | — | — | — |
| Squalane | 1.00 | — | — | — | — |
| Octyldodecanol | 5.00 | — | — | — | — |
| Dextrin palmitate | — | 1.50 | — | — | — |
| Candelilla wax | 3.00 | — | 2.00 | — | — |
| Beeswax | — | 3.00 | 3.00 | — | — |
| Ceresin | 5.00 | — | 1.00 | 1.00 | 1.00 |
| Polyethylene | 5.00 | 3.00 | 5.00 | 3.00 | 3.00 |
| Synthetic wax, Ethylene/propylene copolymer | — | 4.00 | 2.00 | 4.00 | 4.00 |
| Microcrystalline wax | 3.00 | 3.00 | 4.00 | 4.00 | 4.00 |
| Yellow No. 4 Aluminum Lake | — | 0.10 | — | — | — |
| Red No. 201 | 1.40 | — | — | — | — |
| Red No. 202 | 1.10 | 2.00 | 1.60 | — | — |
| Bengara | 1.20 | — | — | 0.36 | 0.36 |
| Red No. 226 | — | — | — | 1.60 | 1.60 |
| Blue No. 1 Aluminum Lake | — | — | 0.10 | — | — |
| Titanium oxide | 0.80 | — | 0.10 | 1.00 | 1.00 |
| Dimethylsilylated silica | — | — | — | 0.50 | 0.50 |
| TiO2 coated mica (pearlescent agent) | 2.50 | — | — | 3.00 | 3.00 |
| Synthetic Fluorphlogopite, titanium oxide, iron oxide (lame luster) | — | — | 0.10 | 0.30 | 0.30 |

TABLE 10-continued

| Ingredient | | Ex. 24 | Ex. 25 | Ex. 26 | Ex. 27 | Com. Ex. 6 |
|---|---|---|---|---|---|---|
| | Borosilicic acid(Ca/Al), silica, titanium oxide, stannous oxide (lame luster) | — | 0.50 | — | — | — |
| | (PET/polymethylmethacryalate) laminate (lame luster) | — | — | 0.40 | — | — |
| Total | | 100.00 | 100.00 | 100.00 | 100.00 | 100.00 |
| Evaluation result | Storage stability | G | G | G | G | G |
| | Applicability (ease of spreading or sliminess) | G | G | G | G | M |
| | Oily feeling and moisturizing ability | G | G | G | G | G |
| | Affinity with the skin and adhesion to the skin | G | G | G | G | B |
| | Gloss after application | G | G | G | G | G |
| | Gloss-holding effect | G | G | G | G | B |
| | Safety to the skin | G | G | G | G | G |

In both Examples 24 and 26, lipsticks were prepared using the ester compound obtained in Preparation Example 2. In both Examples 25 and 27, lipsticks were prepared using the ester compound obtained in Preparation Example 5. All the cosmetics exhibited good properties regardless of the amount of the ester compounds and the kind of other ingredients blended. Meanwhile, in Comparative Example 6, the ester compound obtained in Preparation Example 5 used in Example 27 was changed to the ester compound obtained in Comparative Preparation Example 3, that is, the ester compound which was obtained using isostearic acid having 18 carbon atoms as a fatty acid. The applicability was somewhat lowered and the affinity with the skin and the adhesion to the skin were poor. The gloss-holding effect was also poor in the lipsticks due to the poor properties of the ester compound obtained using isostearic acid.

The ester compound contained in the oily base for a cosmetic of the present invention has the effect that the ester compound may give not only the cosmetic effects which have not been attained by any prior art ester compounds, for example, proper emollient property, moisturizing property and, proper oily feeling without uncomfortable sticky feeling, but also gloss-holding ability, smooth feeling on use, good adhesion to the skin, safety to the skin, good cosmetic effect-holding ability and good storage ability, to a cosmetic. Therefore, the present ester compound is useful for various cosmetics such as skin creams, hair treatments, foundations, mascaras, eye shadows, lip glosses and lipsticks.

The invention claimed is:

1. A cosmetic comprising an oily base comprising ester compounds made from dipentaerythritol and at least one fatty acid selected from the group consisting of fatty acids having 5 to 16 carbon atoms and a molar ratio of a dipentaerythritol residue to a fatty acid residue having 5 to 16 carbon atoms in the ester compound is 1.0:3.0 to 1.0:6.0 the ester compounds comprising at least two esters selected from monoester, diester, triester, tetraester, pentaester, and hexaester of diepentaerythritol and the fatty acid wherein the cosmetic is selected from a foundation, mascara, eye shadow, lip gloss, lip stick, skin cream and a hair treatment composition.

2. The cosmetic according to claim 1, wherein the molar ratio of a dipentaerythritol residue to a fatty acid residue having 5 to 16 carbon atoms is 1.0:3.5 to 1.0:6.0.

3. The cosmetic according to claim 1, wherein the molar ratio of a dipentaerythritol residue to a fatty acid residue having 5 to 16 carbon atoms is 1.0:4.0 to 1.0:6.0.

4. The cosmetic according to claim 1, wherein the fatty acid has 8 to 16 carbon atoms.

5. The cosmetic according to claim 1, wherein the fatty acid has 9 to 16 carbon atoms.

6. The cosmetic according to claim 1, wherein the fatty acid is selected from the group consisting of isononanoic acid, neopentanoic acid, 2-ethylhexanoic acid, neodecanoic acid, isomyristic acid and isopalmitic acid.

7. The cosmetic according to claim 1, wherein the fatty acid is isononanoic acid.

8. The cosmetic according to claim 1, wherein a hydroxyl value of the oily base is 0 to 340.

9. The cosmetic according to claim 1, wherein a hydroxyl value of the oily base is 0.5 to 200.

10. The cosmetic according to claim 1, wherein a hydroxyl value of the oily base is 0.5 to 150.

11. The cosmetic according to claim 1, wherein a saponification value of the oily base is 170 to 450.

12. The cosmetic according to claim 1, wherein a saponification value of the oily base is 175 to 360.

13. The cosmetic according to claim 1, wherein a saponification value of the oily base is 180 to 320.

14. The cosmetic according to claim 1, wherein a viscosity at 25 degrees C. of the oily base is 500 to 40,000 mPa·s.

15. The cosmetic according to claim 1, wherein a viscosity at 25 degrees C. of the oily base is 500 to 24,000 mPa·s.

16. The cosmetic according to claim 1, wherein a viscosity at 25 degrees C. of the oily base is 500 to 20,000 mPa·s.

* * * * *

UNITED STATES PATENT AND TRADEMARK OFFICE
CERTIFICATE OF CORRECTION

| | | |
|---|---|---|
| PATENT NO. | : 8,420,109 B2 | Page 1 of 1 |
| APPLICATION NO. | : 12/850831 | |
| DATED | : April 16, 2013 | |
| INVENTOR(S) | : Naoki Sasaki et al. | |

It is certified that error appears in the above-identified patent and that said Letters Patent is hereby corrected as shown below:

On the Title Page, Item (73)

Please correct the name of the Assignee as follows:

from:   (73) "Kokyo Alcohol Kogyo, Co., Ltd., Chiba (JP)"

to:   (73) --Kokyu Alcohol Kogyo, Co., Ltd., Chiba (JP)--

Signed and Sealed this
Thirteenth Day of August, 2013

Teresa Stanek Rea
*Acting Director of the United States Patent and Trademark Office*